US012226431B2

(12) United States Patent
Jena

(10) Patent No.: US 12,226,431 B2
(45) Date of Patent: Feb. 18, 2025

(54) AEROSOL AND TOPICAL ADMINISTRATION OF A FORMULATION CONTAINING CYCLODEXTRIN, QUERCETIN AND ZINC, IN COMBINATION OR SEPARATELY, TO MITIGATE INFECTION BY ENVELOPED VIRUSES

(71) Applicant: Porosome Therapeutics, Inc., Boston, MA (US)

(72) Inventor: Bhanu Pratap Jena, Bloomfield Hills, MI (US)

(73) Assignee: POROSOME THERAPEUTICS, INC., Boston, MA (US)

( * ) Notice: Subject to any disclaimer, the term of this patent is extended or adjusted under 35 U.S.C. 154(b) by 0 days.

(21) Appl. No.: 17/472,604

(22) Filed: Sep. 11, 2021

(65) Prior Publication Data
US 2023/0082992 A1    Mar. 16, 2023

(51) Int. Cl.
A61K 31/724   (2006.01)
A61K 9/00     (2006.01)
A61K 9/12     (2006.01)
A61K 31/352   (2006.01)
A61K 33/30    (2006.01)
A61K 47/02    (2006.01)
A61K 47/18    (2017.01)

(52) U.S. Cl.
CPC ............ A61K 31/724 (2013.01); A61K 9/008 (2013.01); A61K 9/12 (2013.01); A61K 31/352 (2013.01); A61K 33/30 (2013.01); A61K 47/02 (2013.01); A61K 47/186 (2013.01)

(58) Field of Classification Search
None
See application file for complete search history.

(56) References Cited

U.S. PATENT DOCUMENTS

| | | | |
|---|---|---|---|
| 6,572,849 B2 | 6/2003 | Shahinian, Jr. | |
| 10,195,227 B2 | 2/2019 | Fornoni et al. | |
| 2005/0019380 A1 | 1/2005 | Hoon et al. | |
| 2007/0003516 A1 | 1/2007 | Almond et al. | |
| 2007/0219159 A1 | 9/2007 | Wallace et al. | |
| 2008/0063735 A1* | 3/2008 | Reeve ................. | A61Q 17/005 424/736 |
| 2011/0312985 A1 | 12/2011 | Nahmias et al. | |
| 2012/0251594 A1 | 10/2012 | Longest et al. | |
| 2014/0011854 A1* | 1/2014 | Tyavanagimatt ...... | A61K 47/10 514/410 |
| 2015/0216895 A1 | 8/2015 | McKew et al. | |
| 2018/0360945 A1 | 12/2018 | Wu et al. | |
| 2018/0372751 A1 | 12/2018 | Cravatt et al. | |
| 2019/0191704 A1 | 6/2019 | Albright et al. | |
| 2019/0262385 A1 | 8/2019 | Fornoni et al. | |
| 2021/0228616 A1 | 7/2021 | Fornoni et al. | |
| 2021/0228619 A1 | 7/2021 | Peyman | |
| 2022/0409653 A1 | 12/2022 | Jena | |
| 2023/0357329 A1 | 11/2023 | Jena | |
| 2023/0414650 A1 | 12/2023 | Jena et al. | |
| 2024/0053354 A1 | 2/2024 | Cho et al. | |
| 2024/0316094 A1 | 9/2024 | Jena | |
| 2024/0316152 A1 | 9/2024 | Jena et al. | |

FOREIGN PATENT DOCUMENTS

| | | | |
|---|---|---|---|
| EP | 0300526 A2 | 1/1989 | |
| JP | H0775536 A | 3/1995 | |
| WO | 2010042633 A2 | 4/2010 | |
| WO | 2014022841 A1 | 2/2014 | |
| WO | 2016104967 A1 | 6/2016 | |
| WO | 2017132059 A1 | 8/2017 | |
| WO | 2017216288 A1 | 12/2017 | |
| WO | 2021155323 A1 | 8/2021 | |
| WO | 2021168173 A1 | 8/2021 | |
| WO | 2021180742 A1 | 9/2021 | |
| WO | WO-2021184070 A1 * | 9/2021 | ............ A61K 47/26 |
| WO | WO-2021234362 A1 * | 11/2021 | ........... A61K 31/145 |
| WO | 2022112430 A1 | 6/2022 | |

OTHER PUBLICATIONS

Wilkinson, G. Pharmacokinetics, The Dynamics of Drug Absorption, Distribution, and Elimination (2001). In: Goodman and Gilman's the pharmacological basis of therapeutics. International edition, 10th edition, Mc Grow Hill, 971. (Year: 2001).*

Ali Khan, W., Kumar Verma, D., Azeem Khan, M., Kumar Mohapatra, A., & Kumar Nanda, R. (2021). Zinc 2+ ion inhibits SARS-COV-2 main protease and viral replication in vitro. Chemical Communications, 57(78), 10083-10086. (Year: 2021).*

Abdel-Halim, E. S., et al.; "Cotton fabric finished with β-cyclodextrin: inclusion ability toward antimicrobial agent"; Carbohydrate Polymers, vol. 102, (2014) pp. 550-556.

Anonymous; "Annex to the European Commission guideline on Excipients in the labelling and package leaflet of medicinal products for human use" (SANTE-2017-11668) EMA/CHMP/302620/2017 Rev. 2 (2019).

Berg, O. et al.; "The effects of topical nasal steroids on rat respiratory mucosa in vivo, with special reference to benzalkonium chloride"; Allergy, vol. 52, Issue No. 6 (1997); pp. 627-632.

(Continued)

Primary Examiner — Dale R Miller
(74) Attorney, Agent, or Firm — CANTOR COLBURN LLP

(57) ABSTRACT

The invention provides the use of a formulation containing cyclodextrine, quercetin and zinc, at appropriate concentrations to mitigate infections by enveloped viruses like SARS-COV-2, influenza and HIV/AIDS, when administered via pulmonary and dermal route. While the different forms of cyclodextrin prevent the entry of coated virus into host cells by extracting and sequestering cholesterol molecules at the virus coat and at the host cell plasma membrane, the natural plant-based ionophore quercetin in the formulation, enables cellular entry of zinc, inhibiting viral replication by altering polymerase activity in the host cell. Hence cyclodextrine, and quercetin plus zinc, either in combination or in tandem order of administration, serves both as prophylactic and therapeutic.

26 Claims, No Drawings

(56) References Cited

OTHER PUBLICATIONS

Berg, O., et al.; "The effect of a benzalkonium chloride containing nasal spray on human respiratory mucosa in vitro as a function of concentration and time of action"; Pharmacology & Toxicology, vol. 76, Issue No. 4 (1995); pp. 245-249.

Bertrand, F. et al.; "Phosphorylation of vimentin is an intermediate step in protein kinase C-mediated glycoconjugate secretion"; American Journal of Physiology, vol. 266(3pt1) (1994); pp. C611-C621; DOI: 10.1152/ajpcell.1994.266.3.C611.

Campbell, S. M., et al.; "Lipid rafts and HIV-1: From viral entry to assembly of progeny virions"; Journal of Clinical Virology, vol. 22, (2001) pp. 217-227; DOI: https://doi.org/10.1016/S1386-6532(01)00193-7.

Chen, C., et al.; "Epsin 1 is a cargo-specific adaptor for the clathrin-mediated endocytosis of the influenza virus"; PNAS, vol. 105, (2008) pp. 11790-11795.

Chen, Y., et al.; "Dengue virus infectivity depends on envelope protein binding to target cell heparan sulfate"; Nature Medicine, vol. 3 (1997) pp. 866-871.

Cho, S. J., et al.; "2002 Structure and dynamics of the fusion pores in live GH-secreting cells revealed using atomic force microscopy"; Endocrinology, vol. 143, Issue No. 3; (2002); pp. 1144-1148.

Cho, W. et al.; "EM 3D contour maps provide protein assembly at the nanoscale within the neuronal porosome complex"; Journal of Microscopy, vol. 232, Issue No. 1 (2008); pp. 106-111.

Cho, W. et al.; "Structure, isolation, composition and reconstitution of the neuronal fusion pore"; Cell Biology International, vol. 28 (2004); pp. 699-708.

Choi, H. J., et al.; "Inhibitory effects of quercetin 3-rhamnoside on influenza A virus replication"; European Journal of Pharmaceutical Science, vol. 37 (2009) pp. 329-333; DOI: https://doi.org/10.1016/j.ejps.2009.03.002.

Dabbagh-Bazarbachi, H., et al.; "Zinc ionophore activity of Hepa 1-6 cells to a liposome model"; Journal of Agricultural and Food Chemistry, vol. 62, Issue No. 32 (2014) pp. 8085-8093.

Deng, H., et al.; "Identification of a major co-receptor for primary isolates of HIV-1"; Nature, vol. 381, (1996) pp. 661-666.

Deutschle, T., et al.; "In vitro genotoxicity and cytotoxicity of benzalkonium chloride"; Toxicology In Vitro, vol. 20, Issue No. 8 (2006) pp. 1472-1477; DOI: 10.1016/j.tiv.2006.07.006.

Engel, S., et al.; "Role of endosomes in simian virus 40 entry and infection"; Journal of Virology, vol. 85, (2011) pp. 4198-4211.

Gansukh, E., et al.; "Nature nominee quercetin's anti-influenza combat strategy—Demonstrations and remonstrations"; Reviews in Medical Virology, vol. 27, Issue No. 3, e1930 (2017) DOI: 10.1002/rmv.1930.

Grummt, T., et al.; "Genotoxicity of nitrosulfonic acids, nitrobenzoic acids, and nitrobenzylalcohols, pollutants commonly found in ground water near ammunition facilities"; Environmental and Molecular Mutagenesis 47(2); 2006; pp. 95-106.

Guggino, W. et al.; "New insights into cystic fibrosis: molecular switches that regulate CFTR"; Nature Reviews. Molecular Cell Biology, vol. 7, Issue No. 6 (2006); pp. 426-436.

Ho, et al.; "In vitro effects of preservatives in nasal sprays on human nasal epithelial cells"; American Journal of Rhinology, vol. 22, Issue No. 2 (2008) pp. 125-129; DOI: 10.2500/ajr.2008.22.3154.

Hou, X. et al.; "Proteome of the porosome complexes in human airway epithelia: Interaction with the cystic fibrosis transmembrane conductance regulator (CFTR)"; Journal of Proteomics, vol. 96; 2014; pp. 82-91; DOI:10.1016/j.jprot.2013.10.041.

International Search Report and Written Opinion for International Application PCT/US2023/029733; International Filing Date: Aug. 8, 2023; Date of Mailing: Oct. 27, 2023; 12 pages.

Jansook, P., et al. "Cyclodextrins: Structure, physicochemical properties and pharmaceutical applications"; International Journal of Pharmaceutics, vol. 535 (2018) pp. 272-284; DOI: 10.1016/j.ijpharm.2017.11.018.

Jjingo, C.; "Clinical Review"; Center for Drug Evaluation and Research; Mar. 6, 2017.

Karimova, E., et al. Synthesis and Antiviral Activity of Quercetin Brominated Derivatives; Natural Products Communications, vol. 10 (2015) pp. 1565-1568.

Kim, Y., et al.; "Inhibition of influenza virus replication by plan - derived isoquercetin"; Antiviral Research, vol. 88 (2010) pp. 227-235; DOI: https://doi.org/10.1016/j.antiviral.2010.08.016.

Korhonen, J. T., et al.; "R. Chlamydia pneumoniae entry into epithelial cells by clatherin-independent endocytosis"; Microbial Pathogensis, vol. 52, (2012) pp. 157-164.

Larsen, S. T, et al.; "Investigation of the adjuvant and immunosuppressive effects of benzyl butyl phthalate, phthalic acid and benzyl alcohol in a murine injection model"; Food and Chemical Toxicology, vol. 41, Issue No. 3 (2003) pp. 439-446.

Lee, J-S. et al.; "Neuronal Porosome proteome: Molecular dynamics and architecture"; Journal of Proteomics, vol. 75, Issue No. 13; 2012; pp. 3952-3962; DOI:10.1016/j.jprot.2012.05.017.

Lee, J-S. et al.; "Porosome in astrocytes"; Journal of Cellular and Molecular Medicine, vol. 13, Issue No. 2; 2009; pp. 365-372.

Loftsson, T. et al.; "Cyclodextrins and their pharmaceutical applications"; International Journal of Pharmaceutics, vol. 329 (2007) pp. 1-11; DOI: 10.1016/j.ijpharm.2006.10.044.

Loftsson, T., et al.; "Cyclodextrins in eye drop formulations: enhanced topical delivery of corticosteroids to the eye"; Acta Ophthalmol Scand., vol. 80, Issue No. 2 (2002) pp. 144-150.

Loftsson, T., et al.; "Cyclodextrins in topical drug formulations: theory and practice"; International Journal of Pharmaceutics, vol. 225 Issues No. 1-2 (2001) pp. 15-30; DOI:10.1016/S0378-5173(01)00761-X.

Loftsson, T., et al.; "The effects of organic salts on the cyclodextrin solubilization of drugs"; International Journal of Pharmaceutics, vol. 262 (2003) pp. 101-107; doi: 10.1016/s0378-5173(03)00334-x.

Martens, G. W., et al.; "Hypercholesterolemia impairs immunity to tuberculosis"; Infection and Immunity, vol. 76, (2008) pp. 3464-3472.

Naik, A R., et al.; "Self-assembly and biogenesis of the cellular membrane are dictated by membrane stretch and composition"; The Journal of Physical Chemistry B, vol. 123, (2019) pp. 6997-7005.

Pawlikowska-Pawlega, B., et al.; "Modification of membranes by quercetin, a naturally occurring flavonoid, via its incorporation in the polar head group"; Biochimica Biophysica Acta Biomembranes, vol. 1768 (2007) pp. 2195-2204.

Riechelmann, H., et al.; "Nasal toxicity of benzalkonium chloride"; American Journal of Rhinology, vol. 18, Issue No. 5 (2004) pp. 291-299.

Ryan, W. R, et al.; "Safety of a preservative-free acidified saline nasal spray"; Archives of Autolaryngolical Head and Neck Surgery, vol. 136 (2010) pp. 1099-1103; DOI: 10.1001/archoto.2010.179.

Schneider, S. et al.; "Surface dynamics in living acinar cells imaged by atomic force microscopy: Identification of plasma membrane structures involved in exocytosis"; PNAS, vol. 94; 1997; pp. 316-321.

Smith, D.M.; et al. "Cholesterol reduction in liquid egg yolk using β-cyclodextrin"; Journal of Food Science, vol. 69 (1995) pp. 691-694.

Spear, P. G., et al.; "Three classes of cell surface receptors for alpha herpes virus entry"; Virology, vol. 275 (2000) pp. 1-8.

Steinsvag, S. K., et al.; "Effects of topical nasal steroids on human respiratory mucosa and human granulocytes in vitro"; Acta Otolaryngol Ica, vol. 116, Issue No. 6 (1996) pp. 868-875.

Swiercz, R., et al.; "Pulmonary irritation after inhalation exposure to benzalkonium chloride in rats"; International Journal of Occupational Medicine and Environmental Health, vol. 21, Issue No. 2 (2008) pp. 157-163.

Te Velthuis, A. J. W., et al.; "Zn2+ Inhibits Coronavirus and Arterivirus RNA Polymerase Activity In Vitro and Zinc Ionophores Block the Replication of These Viruses in Cell Culture"; PLOS Pathogens, vol. 6, Issue No. 11 (2010) e1001176; 10 pages.

Vikmon, M.; "Methyl-Cyclodextrin for use in Treating Enveloped Virus Infections Such as SARS-CoV-2"; Cyclodextrin News; Oct. 28, 2021.

(56) References Cited

OTHER PUBLICATIONS

Weerapana, E., et al., "Quantitative reactivity profiling predicts functional cysteines in proteomes," Nature, vol. 468 (2010); pp. 790-795.

Xue, Y., et al. "Distribution and disposition of benzalkonium chloride following various routes of administration in rats"; Toxicology Letters, vol. 148, Issues No. 1-2 (2004) 113-123; doi: 10.1016/j.toxlet.2003.12.068.

Abdel-Rahman, S., et al.; "Single-dose pharmacokinetics of intravenous Itraconazole and hydroxypropyl-β-Cyclodextrin in infants, children, and adolescents"; Antimicrobial Agents and Chemotherapy, (2007) pp. 2668-2673.

Anonymous; "Background Review for Cyclodextrins Used as Excipients"; European Medicines Agency, available online at "http://www.ema.europa.eu/docs/en_GB/document_library/Report/2014/12/WC500177936.pdf" (accessed on Nov. 10, 2016); (2013) 17 pages.

Awad, A. C., et al.; "Composition and functional properties of cholesterol reduced egg yolk"; Poultry Science, vol. 76, Issue No. 4 (1997) pp. 649-653; DOI: https://doi.org/10.1093/ps/76.4.649.

Barth, H., et al.; "Cellular binding of hepatitis C virus envelope glycoprotein E2 requires cell surface heparan sulfate"; Journal of Biological Chemistry, vol. 278, Issue No. 42 (2003) pp. 41003-41012; DOI: 10.1074/jbc.M302267200.

Bose, S., et al. "Role of heparan sulfate in human parainfluenza virus type 3 infection"; Virology, vol. 298, (2002) pp. 73-83; DOI: 10.1006/viro.2002.1484.

Burckhardt, C. J., et al.; Virus movements on the plasma membrane support infection and transmission between cells. PLoS Pathog. vol. 5, Issue No. 11; e1000621; (2009) 9 pages DOI: 10.1371/journal.ppat.1000621.

Byrnes, A P., et al.; "Binding of Sindbis virus to cell surface heparan sulfate"; Journal of Virology, vol. 72, Issue No. 9 (1998) pp. 7349-7356; doi: 10.1128/jvi.72.9.7349-7356.1998.

Campbell, S. M., et al.; "Virion-associated cholesterol is critical for the maintenance of HIV-1 structure and infectivity"; AIDS, vol. 16 (2002) pp. 2253-2261.

Chakraborty, S., et al. "c·Cbl-mediated selective virus-receptor translocations into lipid rafts regulate productive Kaposi's . . . infection in endothelial cells"; J. of Viro., vol. 85 (2011) pp. 12410-12430; DOI: 10.1128/JVI.05953-11.

Chung, C-S., et al.; "Viccania virus penetration requires cholesterol and results in specific viral envelope proteins associated with lipid rafts"; Journal of Virology, vol. 79, (2005) pp. 1623-1634; doi: 10.1128/JVI.79.3.1623-1634.2005.

de Vries, E., et al. "Dissection of the influenza A virus endocytic routes reveals macropinocytosis as an alternative entry pathway"; PLoS Pathogens, vol. 7, e1001329 (2011); DOI: https://doi.org/10.1371/journal.ppat.1001329.

Desplanques, A S., et al.; "Plasma membrane cholesterol is required for efficient pseudorabies virus entry"; Journal of Virology, vol. 376, (2008) pp. 339-345; DOI: https://doi.org/10.1016/j.virol.2008.03.039.

Di Pierro, F. et al.; "Potential clinical benefits of quercetin in the early stage of Covid-19: Results of a second, pilot, randomized, controlled, . . . clinical trial"; Int. J. of Gen. Med., vol. 14 (2021) pp. 2807-2816; doi: 10.2147/IJGM.S318949.

Ehrlich, M., et al.; "Endocytosis by random initiation and stabilization of clathrin-coated pits"; Cell, vol. 118, Issue No. 5 (2004) pp. 591-605; DOI: https://doi.org/10.1016/j.cell.2004.08.017.

Ergoren, M. C., et al.; A pilot study on the preventative potential of cuclodextrin and hydroxytyrosol against SARS-CoV-2 transmission. Acta Biomedica, vol. 91, Supplement 13: e2020022 (2020) DOI: 10.23750/abm.v91i13-S.10817.

Fenyvesi, E., et al.; "Cyclodextrins in Food Technology and Human Nutrition: Benefits and Limitations"; Critical Reviews in Food Science and Nutrition, vol. 56, (2016) pp. 1981-2004.

Ferk, F., et al.; "Benzalkoniumchloride (BAC) and dimethyldioctadecyl-ammonium bromide (DDAB), two common quaternary, . . . relevant concentrations"; Mutagenesis, vol. 22, Issue No. 6 (2007) pp. 363-370; DOI: https://doi.org/10.1093/mutage/gem027.

Foo, W .; "Combating Coronavirus: Key Role of Cyclodextrins in Treatment and Prevention"; PharmaChem, vol. 19; 2020; pp. 13-15.

Garrido, P.; "The Lord of the NanoRings Cyclodextrins and; the battle against SARS-COV-2"; International Journal of Pharmaceutics, vol. 588; 2020.

Geraghty, R. J., et al.; "Entry of alpha herpes viruses mediated by poliovirus receptor-related protein 1 and poliovirus receptor"; Science, vol. 280, (1998) pp. 1618-1620.

Guyader M, et al.; "Role for human immunodeficiency virus type 1 membrane cholesterol in viral internalization"; Journal of Virology, vol. 76, Issue No. 20 (2002) pp. 10356-10364; DOI: https://doi.org/10.1128/jvi.76.20.10356-10364.2002.

Harrison, S. C.; "Mechanism of membrane fusion by viral envelope proteins"; Advances in Virus Research, vol. 64 (2005) pp. 231-261.

Hofmann, T.,et al.; "Influence of preservatives and topical steroids on ciliary beat frequency in vitro"; Archives of Otolaryngology: Head & Neck Surgery, vol. 130, Issue No. 4 (2004) pp. 440-445.

International Search Report for International Application No. PCT/US2022/040749; International Filing Date—Aug. 18, 2022; Date of Mailing—Oct. 28, 2022; 2 pages.

Jena, B. et al.; "Gi regulation of secretory vesicle swelling examined by atomic force microscopy"; PNAS, vol. 94 (1997); pp. 13317-13322.

Jeremic, A. et al.; "Reconstituted Fusion Pore"; Biophysical Journal, vol. 85; 2035-2043 (2003); doi: 10.1016/S0006-3495(03)74631-1.

Jutras, K. I. R., et al.; "Entry of the lymphogranuloma venereum strain of Chlamydia trachomatis into host cell involves cholesterol-rich membrane domains"; Infection and Immunity, vol. 71, (2003) pp. 260-266.

Kapur, S., et al.; "Toxicology of benzyl alcohols: a QSAR analysis"; Chemosphere, vol. 41, Issue No. 10 (2000) pp. 1643-1649.

Loftsson, T., et al.; "Pharmaceutical applications of cyclodextrins: basic science and product development"; Journal of Pharmacy and Pharmacology, vol. 62, Issue No. 11 (2010) pp. 1607-1621; DOI: https://doi.org/10.1111/j.2042-7158.2010.01030.x.

Madenspacher, J. H., et al.; "Dyslipidemia induces opposing effects on intrapulmonary and extrapulmonary host defense through divergent TLR response phenotypes"; J. of Immun., vol. 185 (2010) 1660-1669; DOI: https://doi.org/10.4049/jimmunol.0903501.

Mehrbod, P., et al.; "Experimental validation and computational modeling of anti-influenza effects of quercetin . . . Rapanea melanophloeos"; BMC Complementary and Alternative Med., vol. 19 (2019) pp. 1-11; https://doi.org/10.1186/s12906-019-2774-3.

Mehrbod, P., et al.; "Immunomodulatory properties of quercetin-3-O-α-L-rhamnopyranoside from Rapanea melanophloeos against influenza a virus"; BMC Complementary and Alternative Med., vol. 18, Article 184 (2018) 10 pages; doi: 10.1186/s12906-018-2246-1.

Omari, M.M.A., et al.; "Factors contributing to solubility synergism of some basic drugs with 13-cyclodextrin in ternary molecular complexes"; Journal of Inclusion Phenomena, vol. 54, Issue No. (2006) pp. 159-164.

Pio Di Cagno, M .; "The potential of cyclodextrins as novel active pharmaceutical ingredients: A short overview"; Molecules, vol. 22, Issue No. 1; (2016) doi: 10.3390/molecules22010001.

Puskas, I .; "HPBCD is a unique component in Janssen's COVID-19 vaccine candidate"; Cyclodextrin News; Feb. 25, 2021.

Read, S.A., et al. (2019) "Role of zinc in antiviral immunity"; Advances in Nutrition, vol. 10, Issue No. 4 (2019) pp. 696-710; doi: 10.1093/advances/nmz013.

Schwiebert, E. et al.; "GTP-binding proteins inhibit cAMP activation of chloride channels in cystic fibrosis airway epithelial cells"; PNAS, vol. 89, Issue No. 22 (1992); pp. 10623-10627.

Summerford, C., et al.; "Membrane-associated heparan sulfate proteoglycan is a receptor for adeno-associated virus type 2 virions"; Journal of Virology, vol. 72, Issue No. 2 (1998) pp. 1438-1445; doi: 10.1128/jvi.72.2.1438-1445.1998.

Teixeira, S. M., et al.; "Chlorhexidine: Bet·· cyclodextrin inhibits yeast growth by extraction of ergosterol"; Brazilian Journal of Microbiology, vol. 43, Issue No. 2 (2012) pp. 810-818, ISSN 1517-8382; DOI: 10.1590/S1517-83822012000200047.

(56) References Cited

OTHER PUBLICATIONS

Written Opinion of the International Searching Authority for International Application No. PCT/US2022/040749; International Filing Date—Aug. 18, 2022; Date of Mailing—Oct. 28, 2022; 2 pages.
"The Study of Quadruple Therapy Zinc, Quercetin, Bromelain and Vitamin C on the Clinical Outcomes of Patients Infected with COVID-19"; https://www.clinicaltrials.gov/study/NCT04468139?term=quercetin,%20zinc&cond=Viral%20Infection&rank=1; 9 pgs (2020).
Barati, F. et al.; "Potential Drugs and Remedies for the Treatment of COVID-19: a Critical Review"; (Abstract) Biological Procedures Online, vol. 22, Issue No. 1; 17 pages; DOI:10.1186/S12575-020-00129-1 (2020).
Bellavite, P.; "Reappraisal of Dietary Phytochemicals for Coronavirus Infection: Focus on Hesperidin and Quercetin"; IntechOpen, pp. 1-51; DOI: 10.5572/intechopen.95529 (2021).
Extended European Search Report for Application 24167332.6 dated Jul. 22, 2024; 15 pages.
Fatmi, S. et al.; "The Use of Cyclodextrin or its Complexes as a Potential Treatment Against the 2019 Novel Coronavirus: A Mini-Review" (Abstract only) vol. 18, Issue No. 4; pp. 382-386 (2021).
Pawar, A. et al.; "Molecular and functional resemblance of dexamethasone and quercetin: A paradigm worth exploring in dexamethasone-nonresponsive COVID-19 patients"; Physiotherapy Research, vol. 34, Issue No. 12; pp. 3085-3088 (2020).
Wilkinson, G.; "Pharmacokinetics"; The Dynamics of Drug Absorption, Distribution, and Elimination, International Edition, McGraw Hill; 2001; 6 pages.

\* cited by examiner

AEROSOL AND TOPICAL ADMINISTRATION OF A FORMULATION CONTAINING CYCLODEXTRIN, QUERCETIN AND ZINC, IN COMBINATION OR SEPARATELY, TO MITIGATE INFECTION BY ENVELOPED VIRUSES

CROSS-REFERENCE TO RELATED APPLICATIONS

The present application claims is a continuation in part application of U.S. patent application Ser. No. 17/207,250, filed on Mar. 19, 2021, which claims the benefit of U.S. Provisional Patent Application Ser. Nos. 63/029,458, filed May 23, 2020, and 63/019,312 filed May 2, 2020, and further claims the benefit of U.S. Provisional Patent Application Ser. No. 63/235,772, filed on Aug. 22, 2021, each of which is hereby incorporated by reference herein in their entireties.

FIELD OF THE INVENTION

The present application generally relates to medicine and, more particularly, to an inhalation and topical use of a formulation containing cyclodextrin, quercetin, and zinc to mitigate infection by enveloped viruses such as HIV and SARS-cov-2.

DISCUSSION OF ART

Viruses enter hosts via the epithelium. The cell plasma membrane of skin and lung epithelia is the first line of defense and when breached, serves as the portal for viral entry into hosts. Studies in the past two decades report the various cell membrane binding and entry mechanisms utilized by viruses to infect. Irrespective of the different mechanisms involved in viral entry into host cells, the initiating critical process is binding of the virus to the cell plasma membrane. Without binding of virus to the cell plasma membrane, there would be no viral entry into the host.

A large number of studies have established that binding of viruses to the cell plasma membrane is subjected to the presence of docking sites or receptors and their regulation by membrane lipid composition and distribution such as the establishment of domains called rafts. Our recent study involving cellular membrane biogenesis, demonstrate that changes in composition of membrane cholesterol, impacts both the chemistry and distribution of plasma membrane proteins and lipids, impacting cell function.

In agreement, recent studies demonstrate that depletion of plasma membrane cholesterol in host cells using M-BCD, significantly reduces entry of the pseudorabies and vaccinia virus into cells. Similarly, studies demonstrate that HIV infectivity is critically dependent on cholesterol. Cholesterol microdomains, called lipid 'rafts', have been suggested in the cellular entry or infection of HIV, its assembly, and its release from infected cells. Studies further report that plasma membrane cholesterol is also required for a wide range of both bacterial and yeast infections. Furthermore, high-cholesterol diet impairs pulmonary host defense against gram-negative bacteria and *Mycobacterium tuberculosis*. Taken together, these results support that CD-mediated depletion of plasma membrane cholesterol in epithelial cells i.e., skin, nasal passage and lung epithelia in humans, using topological application, aerosol spray and nebulization, will mitigate both viral entry and secondary bacterial and yeast infections.

CDs are a family of cyclic oligosaccharides constituted of a macrocyclic ring of glucose subunits joined by $\alpha$-1,4 glycosidic bonds. CDs are used for improving the water-solubility and bioavailability of a wide range of drugs. The U.S. Food and Drug Administration (FDA) has approved the use of cyclodextrins since 2001. Cyclodextrins were first employed in the food industry in the 1970s, and since they have been used as food additives for carrying food-related lipophiles such as vitamins, aromas and colorants. $\beta$CD has also been used as a cholesterol-reducing agent in food of animal origin such as milk and egg. The first pharmaceutical patent related to CDs and pharmaceutical applicability as complexing agents is dated 1953. Currently, cyclodextrins are employed in pharmaceutical products primarily to increase water solubility of poorly soluble drug formulations and to enhance drug bioavailability. Pharmaceutical products containing CDs comprise nasal spray, oral solutions, solid dosage forms, ocular and dermal formulations, suppositories, and parenteral solutions.

Currently, more than 40 pharmaceutical products containing CDs are available in the market worldwide, and the vast majority of them utilize $\beta$CD and its derivatives having higher water solubility such as HP$\beta$CD, M$\beta$CD, and SBE$\beta$CD. Most of the $\beta$CD are also approved by the European Medical Agency for all human administration pathways. CDs are used for example in tablets, aqueous parenteral solutions, nasal sprays and eye drop solutions.

Examples of the use of cyclodextrins in medicines on the European market are $\beta$-CD in cetirizine tablets and cisapride suppositories, y-CD in minoxidil solution, and examples of the use of $\beta$-cyclodextrin derivatives are SBE-$\beta$-CD in the intravenous antimycotic voriconazole, HP-$\beta$-CD in the antifungal itraconazole, intravenous and oral solutions, and RM-$\beta$-CD in a nasal spray for hormone replacement therapy by 17$\beta$-estradiol. In Germany and Japan there are infusion products on the market, containing alprostadil (prostaglandin E1, PGE1) with $\alpha$-CD. Cyclodextrins are currently not included in the European Commission Guideline on excipients in the label and package leaflet of medicinal products for human use. CDs in combination with quercetin and zinc, or used separately in tandem order (CDsfollowed by Quercetin+Zn), either via pulmonary or dermal route, have never been used as an anti-viral drug until now, as presented here in this application.

BRIEF DESCRIPTION OF THE INVENTION

Embodiments of the invention provide the use of a formulation containing cyclodextrin, quercetin and zinc, at appropriate concentrations to mitigate infections by enveloped viruses like SARS-COV-2, influenza and HIV/AIDS. While the different forms of cyclodextrin prevent the entry of coated virus into host cells by extracting and sequestering cholesterol molecules at the virus coat and at the host cell plasma membrane, the natural plant-based ionophore quercetin in the formulation, enables cellular entry of zinc, inhibiting viral replication by altering polymerase activity in the host cell.

Using the non-toxic U.S. Food and Drug Administration (FDA)-approved excipient cyclodextrin as a drug in phosphate buffered saline solutions, will allow the extraction of cholesterol molecules from enveloped virus membranes and the host cell membrane, altering their respective lipid and protein composition and distribution, preventing virus entry into host cells. Using quercetin, a naturally occurring plant-based over the counter zinc ionophore, will enable the cellular entry of zinc to protect host cells against the virus by inhibiting RNA binding, RNA synthesis, viral polyprotein cleavage, viral replication, and viral protease enzyme inactivation, among others. Administration of cyclodextrin alone followed by quercetin and zinc administration or the two combined, in a water based soluble formulation, prevents both viral entry and replication in host cells.

Aerosol spray and nebulization of the combined cyclodextrin, quercetin and zinc, or their tandem administration as a aqueous phosphate buffered saline pH 7.5 solution containing 0.01% Benzalkonium chloride as preservative, will be used to protect the airways including lungs from all coat virus infections. Similarly, topical application of the combined cyclodextrin, quercetin and zinc in aqueous phosphate buffered saline pH 7.5 solution containing 0.01% Benzalkonium chloride as preservative, will be used to protect body surface (skin) from all coated virus infection. Additionally, application to both sides of cellulose masks of the combined cyclodextrin, quercetin and zinc aqueous phosphate buffered saline pH 7.5 solution containing 0.01% Benzalkonium chloride as preservative, will further protect the airways including lungs from all coated virus infection. In such medicated masks, any airborne droplets containing the virus will be neutralized on contact with the medicated mask. This is the first direct use of cyclodextrin, quercetin and zinc as an anti-viral, anti-bactericidal and anti-fungal drug, either in combination or used separately in tandem order (CDs followed by quercetin+Zn) via pulmonary or dermal route.

DETAILED DESCRIPTION OF THE INVENTION

In this study we report that cells exposed to an increasing concentration of methyl beta cyclodextrin (M-βCD) to deplete cholesterol from the cell plasma membrane demonstrate loss in the uptake of phosphatidyl serine by the cell plasma membrane, while the uptake of phosphatidylethanolamine remain unchanged. Similarly, the loss of cholesterol from the cell plasma membrane resulted in the depletion of membrane fusion proteins such as syntaxin and SNAP25 from the plasma membrane suggesting altered membrane fusogenicity. Therefore, changes to the chemistry of the epithelial cell plasma membrane via depletion of sterols/cholesterol by cyclodextrins (CDs), could dictate both the binding of the virus at the cell plasma membrane, and influence both the efficacy and potency of its entry into the host cell.

Formulation is adapted for both surface use and introduction to a subject by dispersal, utilizing any known method of measured nasal sprays or inhalers, wet wipes and medicated masks. The formulation is introduced in form of an aqueous phosphate buffered saline pH 7.5 solution, containing 0.01% Benzalkonium chloride as preservative and different concentrations of the active ingredients: 1-5% cyclodextrin; the flavonoid quercetin, a naturally occurring zinc ionophore at a concentration of 8 ug/ml; and 1 mg/ml zincchloride. Depending on requirement, pH 2.5 citrate buffered aqueous will also be used, where the low pH serves as a preservative and a solvent for cyclodextrin. The active ingredient cyclodextrin (CD) is currently being used as an excipient in pharmaceutical products including in nasal sprays. The U.S. Food and Drug Administration (FDA) has approved the use of CDs since 2001. CDs were first employed in the food industry in the 1970s, and since they have been used as food additives for carrying food-related lipophiles such as vitamins, aromas and colorants. The first pharmaceutical patent related to CDs and pharmaceutical applicability, was made in 1953 to serve as a complexing agents. Pharmaceutical products containing CDs comprise nasal spray, oral solutions, solid dosage forms, ocular and dermal formulations, suppositories, and parenteral solutions. Currently, more than 40 pharmaceutical products containing CDs are available in the market worldwide, and the vast majority of them utilize βCD and its derivatives having higher water solubility such as HPβCD, MβCD, and SBEβCD. Most of the βCD are also approved by the European Medical Agency for all human administration pathways.

Zinc is an essential trace element supporting growth, development and immune health. Zinc is also known to protect against viruses by inhibiting RNA binding, RNA synthesis, viral polyprotein cleavage, viral replication, and viral protease enzyme inactivation. Zinc, however, needs to enter the host cell to protect against the virus. Quercetin, a naturally occurring plant-based over the counter zinc ionophore, will enable the cellular entry of zinc to protect host cells against the virus. Furthermore, quercetin has shown therapeutic effects against influenza virus. Additionally, in silica modelling of the interactions between the SARS-COV-2 Viral Spike Protein and the epithelial cell Angiotensin Converting Enzyme-2 (ACE2) protein, has identified quercetin from a database of 8,000 small molecule candidates of known drugs, metabolites, and natural products, as one of the top 5 most potent compounds for binding to the interface site, and disrupt initiation of viral infection.

Benzalkonium chloride widely used as a preservative in nasal sprays and nebulization, has been reported to cause sino-nasal mucosal injury, nasal squamous metaplasia, ciliary dysmotility, genotoxicity, and other adverse effects (45-47}. Data also suggests the toxic effects of phenylcarbinol, another commonly used preservative (48-50). Despite this evidence, these preservatives continue to be used at higher concentrations even in over the counter preparations. Acidification (pH 2.5) of nasal, inhalable, and topical ophthalmic preparations have been demonstrated to maintain sterility without the need for preservatives. This approach of lowering the pH of the formulated CD and quercetin solutions to be used in wipes and aerosol sprays, will preclude the use of harmful preservatives at higher concentrations, without compromising sterility of the formulation. Therefore, either low concentration of benzalkonium chloride and or low pH formulations will be prepared for use.

Natural CDs such as αCD, βCD, and γCD are hydrophilic in aqueous solutions, however they tend to self-assemble and form complexes. To overcome this limitation, soluble βCD derivatives such as 2-hydroxypropyl-βCD (HPI3CD) and sulfobutylether βCD sodium salt (SBEβCD), are preferred for use in aqueous pharmaceutical formulations. Studies report that inorganic acids such as phosphoric and citric acid induce CD solubilization.

Therefore, embodiments of the present CD formulation will utilize FDA approved concentrations of CDs, quercetin and zinc in buffered solutions to retain both high solubility and sterility. Mode of administration will be through aerosol spray and nebulization, and topical application on body surface using a water-based solution adsorbed to paper, cellulose or fabric. The topical application on body surfaces will including the face and neck, to mitigate envelop virus (such as SARS-COV-2, influenza and HIV), bacteria and fungus infections.

As a proof, recent clinical studies separately using CDs and quercetin on humans, some using randomized, controlled and open label clinical trial, show 98%-100% effective in providing protection from SARS-COV-2 infection as determined using RT-qPCR. These studies show that 98% of SARS-COV-2 infected patients were cleared of the virus in just two weeks of receiving the quercetin treatment.

The invention claimed is:

1. A composition for administration to a subject, for inhibiting viral entry and replication of an enveloped virus in cells of the subject, consisting of:
   1-5% cyclodextrin;
   a zinc ionophore;
   a zinc-containing compound;
   a preservative; and,
   an aqueous buffer.

2. The composition of claim 1, wherein:
   the zinc-containing compound is zinc chloride.

3. The composition of claim 2, wherein:
   the zinc ionophore is quercetin.

4. The composition of claim 3, wherein:
   the quercetin is at a concentration of 8 ug mL-1; and
   the zinc chloride is at a concentration of 1 mg mL-1.

5. The composition of claim 2, where the preservative is 0.01% benzalkonium chloride.

6. The composition of claim 2, wherein:
   the composition is citrate buffered at a pH of 2.5.

7. The composition of claim 2, wherein:
   the composition is phosphate buffered at pH 7.5 and the preservative is 0.01% benzalkonium chloride.

8. The composition of claim 1, wherein:
   the composition is administered as at least one of a nasal spray, an inhalation, a wipe, an aerosol spray, and/or topically.

9. The composition of claim 1, wherein:
   the enveloped virus is at least one of HIV, influenza and/or SARS-COV-2.

10. The composition of claim 1, wherein:
    the enveloped virus is SARS-COV-2.

11. A method of treating a subject at risk of contracting a viral infection, caused by an enveloped virus, the method comprising the step of:
    administering to the subject a composition consisting of 1-5% cyclodextrin, quercetin, zinc chloride, a preservative, and an aqueous buffer.

12. The method according to claim 11, wherein:
    the quercetin is at a concentration of 8 ug mL$^{-1}$; and
    the zinc chloride is at a concentration of 1 mg mL$^{-1}$.

13. The method according to claim 11, wherein:
    the preservative is 0.01% benzalkonium chloride.

14. The method according to claim 11, wherein:
    the composition is citrate buffered at a pH of 2.5.

15. The method according to claim 11, wherein:
    the composition is phosphate buffered at pH 7.5 and the preservative is 0.01% benzalkonium chloride.

16. The method according to claim 11, wherein:
    the composition is administered to the subject as a nasal spray.

17. The method according to claim 11, wherein:
    the composition is administered as an inhalation.

18. The method according to claim 11, wherein:
    the composition is administered topically to a face and/or neck of the subject.

19. The method according to claim 11, wherein:
    the enveloped virus is at least one of HIV, influenza and/or SARS-COV-2.

20. A method of treating a subject at risk of contracting a viral infection, caused by an enveloped virus, the method comprising the step of:
    administering to the subject a first composition consisting of 1-5% cyclodextrin, a preservative, and an aqueous buffer; and,
    administering separately, or coadministering, a second composition consisting of quercetin, a zinc-containing compound, a preservative, and an aqueous buffer.

21. The method according to claim 20, wherein: the second composition is administered to the subject subsequent to administration of the first composition to the subject.

22. The method according to claim 20, wherein:
    the zinc-containing compound is zinc chloride at a concentration of 1 mg mL$^{-1}$;
    wherein the quercetin is at a concentration of 8 µg mL$^{-1}$.

23. A composition for administration to a subject, for inhibiting viral entry and replication of an enveloped virus in cells of the subject, consisting of:
    methyl beta-cyclodextrin (M-ßCD);
    quercetin;
    a zinc-containing compound;
    a preservative; and,
    an aqueous buffer.

24. The composition of claim 23, wherein:
    the zinc-containing compound is zinc chloride.

25. The composition of claim 24, wherein:
    the quercetin is at a concentration of 8 ug mL$^{-1}$; and
    the zinc chloride is at a concentration of 1 mg mL$^{-1}$.

26. A composition for administration to a subject, for inhibiting viral entry and replication of an enveloped virus in cells of the subject, consisting of:
    2-hydroxypropyl-ßCD;
    quercetin;
    a zinc-containing compound;
    a preservative; and,
    an aqueous buffer.

* * * * *